(12) United States Patent
Thallapalli et al.

(10) Patent No.: US 6,730,704 B2
(45) Date of Patent: May 4, 2004

(54) 1-(ARYLOXY)PROPIONOYL-2-ARYLSULFONYL HYDRAZINES, PROCESS FOR PREPARATION THEREOF AND USE THEREOF AS HYPOGLYCEMIC AGENTS

(75) Inventors: Ramalingam Thallapalli, Hyderabad (IN); Venkata Durga Nageswar Yadavalli, Hyderabad (IN); Ramakrishna Sistla, Hyderabad (IN); Adari Bhaskar Rao, Hyderabad (IN); Prakash Vamanrao Diwan, Hyderabad (IN); Jhillu Singh Yadav, Hyderabad (IN); Kondapuram Vijaya Raghavan, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 49 days.

(21) Appl. No.: 10/108,925

(22) Filed: Mar. 29, 2002

(65) Prior Publication Data

US 2003/0187065 A1 Oct. 2, 2003

(51) Int. Cl.$^7$ .................. A01N 41/06; A61K 31/18
(52) U.S. Cl. .......................... 514/604; 564/81
(58) Field of Search ................. 514/604; 564/81

(56) References Cited

FOREIGN PATENT DOCUMENTS

GB          1041982      *   9/1966

OTHER PUBLICATIONS

Nageswar et al., Chem. Abs. 110:212780.*

D, Finley et al., "Ubiquitination" Annu. Rev. Cell Biol., vol. 7, (1991), pp. 25–69.

M. Hochstrasser, "Ubiquitin and Intracellular Protein Degradation" Current Opinion in Cell Biology, vol. 4, (1992), pp. 1024–1031.

D. Lindsey et al., "A Deubiquitinating Enzyme That Disassembles Free Polyubiquitin Chains is Required for Development But Not Growth in Dictyostelium" The Journal of Biological Chemistry, vol. 273, No. 4, Oct. 30, 1998, pp. 29178–29187.

I. Rose, "Role of Ubiquitin–Protein Isopeptidase Action in Protein Breakdown" Current Communications in Molecular Biology, (1988), Schlesinger and Hershko (eds.),Cold Spring Harbor Laboratory, New York, pp. 111–114.

* cited by examiner

*Primary Examiner*—Peter O'Sullivan
(74) *Attorney, Agent, or Firm*—Sughrue Mion, PLLC

(57) ABSTRACT

The present invention relates to 1-(aryloxy)propionoyl-2-arylsulfonyl hydrazines useful as hypoglycemic agents, and to a process for synthesis thereof. The present invention also relates to the synthesis of 1-(aryloxy)propionoyl-2-arylsulfonyl hydrazines as new hypoglycemic agents which may be useful in the treatment of diabetes.

17 Claims, 2 Drawing Sheets

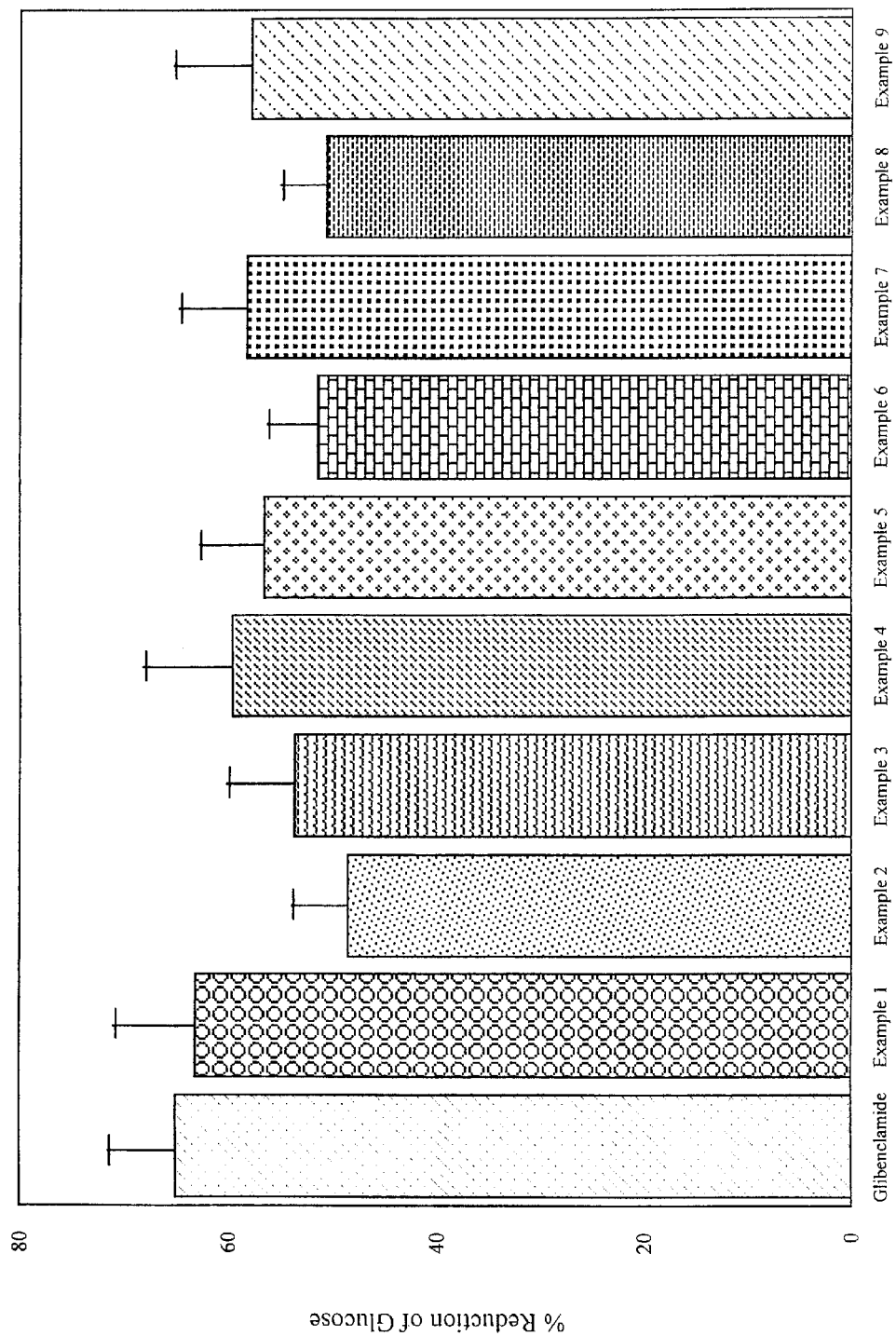

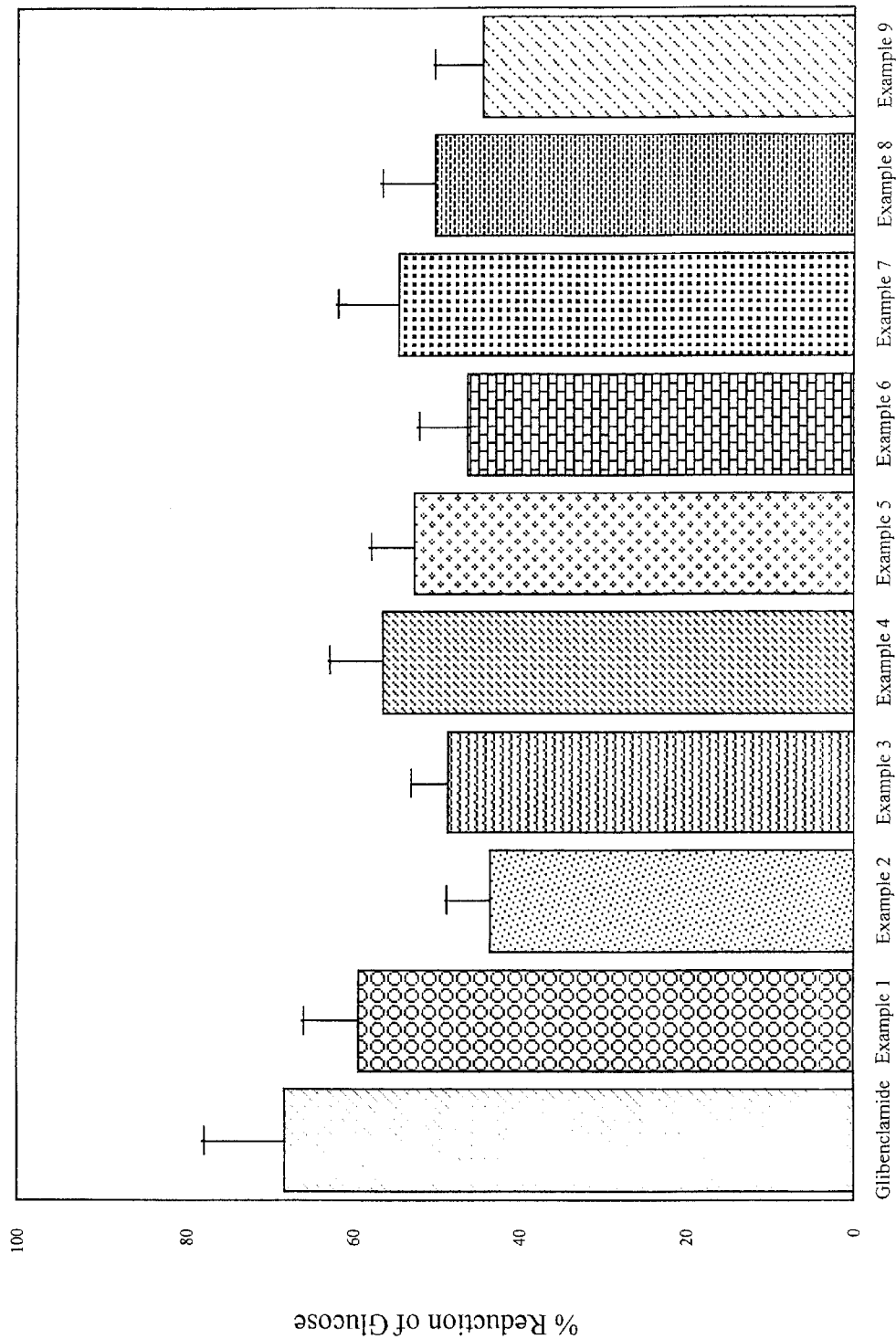
Fig. 2: Hypoglycemic activity of 1-(aryloxy)propionoyl-2-arylsulfonyl hydrozines in Sreptozotocin induced diabetic rats

1-(ARYLOXY)PROPIONOYL-2-ARYLSULFONYL HYDRAZINES, PROCESS FOR PREPARATION THEREOF AND USE THEREOF AS HYPOGLYCEMIC AGENTS

FIELD OF THE INVENTION

The present invention relates to 1-(aryloxy)propionoyl-2-arylsulfonyl hydrazines useful as hypoglycemic agents, and to a process for synthesis thereof The present invention also relates to the synthesis of 1-(aryloxy)propionoyl-2-arylsulfonyl hydrazines as new hypoglycemic agents which may be useful in the treatment of diabetes.

BACKGROUND OF THE INVENTION

Introduction of more clinically effective hypoglycemic agents has been followed invariably by the rapid emergence of resistant antidiabetic drugs leading to increasing demand for new and potent hypoglycemic drugs. Acquisition of resistance has seriously reduced the therapeutic value of many known drugs including antidiabetics and has become a major stimulus to look for new moieties. Hence, the best approach is to look for new molecules structurally different from the existing drugs. The present invention relates to such an effort in developing title compounds as new hypoglycemic agents. These have not so far been investigated for the hypoglycemic activity and all compounds described are new molecules reported for the first time.

Reference may be made to Indian Drugs, 17, 315, 1980, wherein, authors have synthesized arylsulfonyl hydrazines as hypoglycemic agents. The drawbacks are that no substitutions were made to the hydrazine group which can improve the hypoglycemic activity. Incorporation of aryloxyalkyl substituents to organic moieties has been found to result in compounds which possess enhanced biological profile. Reference may also be made to Indian J. Chem:27B, 1057–1059, 1988, wherein authors have introduced substitutions by condensation of 4-chlorophenoxyacetic and isobutyric acid hydrazides with arylsulfonyl chlorides.

OBJECTS OF THE INVENTION

The main object of the present invention is to provide 1-(aryloxy)propionoyl-2-arylsulfonyl hydrazines which obviates the drawbacks as detailed above.

Another object of the present invention is to provide a process for the synthesis of 1-(aryloxy)propionoyl-2-arylsulfonyl hydrazines as potential hypoglycemic agents.

Still another object of the present invention is to unravel new hypoglycemic molecules structurally different from the known drugs such as Glibenclamide, Tolbutamide, Chloropropamide, Phenformin, Metformin, etc.

SUMMARY OF THE INVENTION

In the present invention, aryloxypropionic acid hydrazides were reacted with arylsulfonyl chlorides to obtain the title compounds as hypoglycemic agents for the first time.

Accordingly the present invention relates to 1-(aryloxy)propionoyl-2-arylsulfonyl hydrazine of the formula

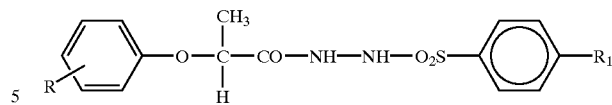

wherein R is selected from 4-Cl, 3-$CH_3$-4-Cl and 2,4-$Cl_2$, $R_1$ is selected from H, Cl, and $CH_3$.

In another embodiment of the invention, the 1-(aryloxy)propionoyl-2-arylsulfonyl hydrazine are selected from the following

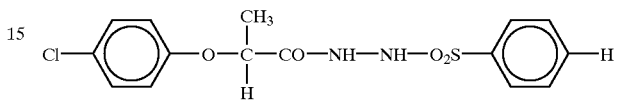

1-(aryloxy)propionoyl-2-arylsulfonyl hydrazine of the formula

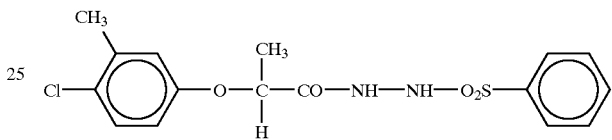

1-(aryloxy)propionoyl-2-arylsulfonyl hydrazine of the formula

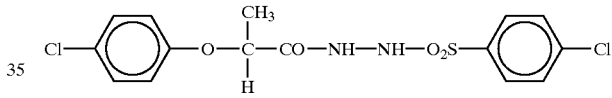

1-(aryloxy)propionoyl-2-arylsulfonyl hydrazine of the formula

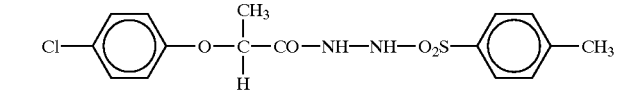

1-(aryloxy)propionoyl-2-arylsulfonyl hydrazine of the formula

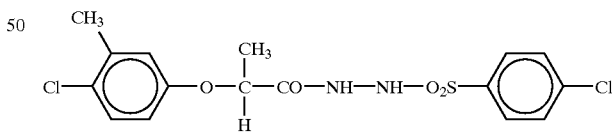

1-(aryloxy)propionoyl-2-arylsulfonyl hydrazine of the formula

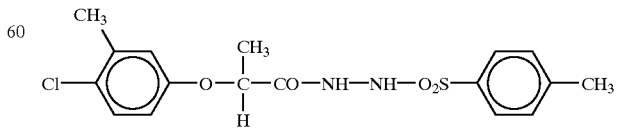

1-(aryloxy)propionoyl-2-arylsulfonyl hydrazine of the formula

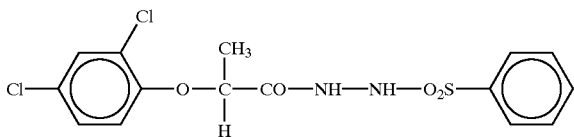

1-(aryloxy)propionoyl-2-arylsulfonyl hydrazine of the formula

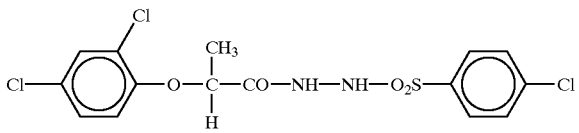

1-(aryloxy)propionoyl-2-arylsulfonyl hydrazine of the formula

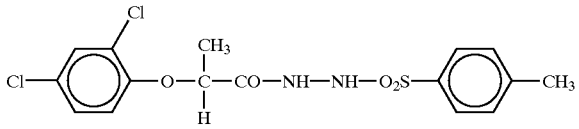

The present invention also provides a process for the synthesis of 1-(aryloxy)propionoyl-2-arylsulfonyl hydrazines useful as new oral hypoglycemic agents, which comprises reacting an aryloxypropionic acid hydrazide with an arylsulfonyl chloride.

In an embodiment of the present invention, aryloxy is selected from the group consisting of 4-chlorophenoxy, 3-methyl-4-chlorophenoxy and 2,4-dichlorophenoxy groups.

In another embodiment of the present invention, aryl is selected from the group consisting of phenyl, 4-chlorophenyl and 4-tolyl.

BRIEF DESCRIPTION OF THE ACCOMPANYING DRAWINGS

FIG. 1 shows the hypoglycemic activity of 1-(aryloxy) propionoyl-2-arylsulfonyl hydrozines in normoglycemic rats.

FIG. 2 shows the hypoglycemic activity of 1-(aryloxy) propionoyl-2-arylsulfonyl hydrozines in Sreptozotocin induced diabetic rats.

DETAILED DESCRIPTION OF THE INVENTION

These 1-(aryloxy)propionoyl-2-arylsulfonyl hydrazines are new molecules synthesized for the first time possessing hypoglycemic activity orally.

The hydrazides, i.e. 4-chlorophenoxypropionic acid hydrazide, 3-methyl-4-chlorophenoxypropionic acid hydrazine and 2-4-dichlorophenoxypropionic acid hydrazide which are required for the synthesis of title compounds were prepared from 4-chlorophenol, 3-methyl-4-chlorophenol and 2,4-dichlorophenol respectively.

The following examples are given by way of illustration and therefore should not be constructed to limit the scope of the present invention.

EXAMPLE 1

1-(4'-Chlorophenoxy)propionoyl-2-phenylsulfonyl Hydrazine

To a solution of 4-chlorophenoxypropionic acid hydrazide in dry pyridine, benzenesulfonyl chloride was added dropwise and the reaction mixture refluxed, for 6 hours. The reaction product was poured over crushed ice and the separated organic solid was filtered and crystallized from ethanol to give the title compound which was confirmed by spectroscopic data.m.p. 127–129° C. $^1$H NMR (CDCl$_3$+DMSO-d6): 1.25 (d), 3H, J=8.8 Hz), 4.60 (q, 1H, J=6.8 Hz), 6.70 (d, 2H, J=7.2 Hz), 7.20 (d, 2H, J=7.0 Hz), 7.45 (t, 2H, J=7.0 Hz), 7.60 (t, 1H, J=70 Hz), 7.75 (d, 2H, J=7.2 Hz), 9.65 (brs, 1H) 10.40 (brs, 1H).

EXAMPLE 2

1-(4'-Chlorophenoxy)propionoyl-2-(4"-chlorophenyl)sulfonyl Hydrazine

4-Chlorophenoxypropionic acid hydrazide was dissolved in dry pyridine. To this solution, 4-Chlorobenzenesulfonyl chloride was added slowly while stirring. The contents were refluxed for 7 hours. Then cooled and poured over crushed ice when the crude product was obtained. It was filtered, washed with water, dried and crystallized from ethanol to give the title compound, which was confirmed by spectral data. M.p. 132–134° C. $^1$H NMR (CDCl$_3$+DMSO-d6): 1.60 (d, 3H, J=6.6 Hz), 4.75 (1, 1H, J=6.6 Hz), 6.90 (d, 2H, J=7.5 Hz), 7.20 (d, 2H, J=7.5 Hz), 7.5 (d, 2H, J=7.6 Hz), 7.90 (d, 2H, J=7.6 Hz), 9.88 (brs, 1H) 10.25 (brs, 1H).

EXAMPLE 3

1-(4'-Chlorophenoxy)propionoyl-2-(4"-toluene) sulfonyl Hydrazine

To a solution of 4-chlorophenoxypropionic acid hydrazide in dry pyridine, 4-toluenesulfonyl chloride was added dropwise and the reaction mixture was refluxed for 5 hours. Crude reaction product was obtained after pouring the contents in ice water. It was filtered, washed with water and crystallized from ethanol to give above compound. Pure product was confirmed by spectroscopic data. m.p. 162–164° C. $^1$H NMR (CDCl$_3$+DMSO-d6): 1.35 (d, 3H, J=6.8 Hz), 2.40 (s, 3H), 4.60 (1, 1H, J=6.8 Hz), 6.80 (d, 2H, J=7.4 Hz), 7,16 (d, 2H, J=7.4 Hz), 7.50 (d, 2H, J=7.5 Hz), 7.80 (d, 2H, J=7.5 Hz), 9.10 (brs, 1H), 10.20 (brs, 1H).

EXAMPLE 4

1-(3'-Methyl-4'-chlorophenoxy)propionoyl-2-phenylsulfonyl Hydrazine

3-Methyl-4-chlorophenoxypropionic acid hydrazide was added to dry pyridine to make uniform solution. Benzenesulfonyl chloride was added dropwise while stirring. Later, the reaction mixture was refluxed for 6 hours. The crude product was obtained when the reaction mixture was poured over crushed ice. It was filtered, washed with good amount of water, dried and crystallized from ethanol to give the above compound whose structure was confirmed by spectroscopic data. m.p. 148–149° C. $^1$H NMR (CDCl$_3$+DMSO-d6): 1.35 (d, 3H, J=6.8 Hz), 2.34 (s, 3H), 4.52 (q, 1H, J=6.8 Hz), 6.58 (dd, 1H, J=7.3 & 2.1 Hz), 6.78 (d, 1H, J=2.0 Hz), 7.16 (d, 1H, J=7.4 Hz), 7.40 (t, 2H, J=7.3 Hz), 7.55 (t, 1H, J=7.3 Hz), 7.75 (d, 2H, J=7.4 Hz), 9.10 (brs, 1H), 10.15 (brs, 1H).

EXAMPLE 5

1-(3'-Methyl-4'-chlorophenoxy)propionoyl-2-(4"-chlorophenyl)sulfonyl Hydrazine

To a solution of 3-methyl-4-chlorophenoxypropionic acid hydrazine in hot dry pyridine, 4-chlorobenzenesulfonyl chloride was added slowly while stirring. Then, the reaction mixture was refluxed for 8 hours. The crude product gets separated when the reaction medium was poured over ice water. It was filtered, washed with excess of water, dried and crystallized from ethanol to give the title compound. Structure of the compound was confirmed by spectral data. m.p. 164–166° C. $^1$H NMR (CDCl$_3$+DMSO-d6): 1.36 (d, 3H, J=6.5 Hz) 2.35 (s, 3H), 4.60 (1, 1H, J=6.5 Hz), 6.60 (dd, 1H, J=7.0 & 1.8 Hz), 6.78 (d, 1H, J=6.8 Hz), 7.18 (d, 1H, J=7.0 Hz), 7.38 (d, 2H, J=7.8 Hz), 7.70 (d, 2H, J=7.8 Hz), 9.78 (brs, 1H) 10.30 (brs, 1H).

EXAMPLE 6

1-(3'-Methyl-4'-chlorophenoxy)propionoyl-2-(4"-tolune)sulfonyl Hydrazine

3-Methyl-R-chlorophenoxypropionic acid hydrazide was dissolved in dry pyridine. 4-tolunesulfonyl choloride was then added dropwise while stirring. Later reaction mixture was refluxed for 6 hours, cooled and poured over ice water. Crude product thus obtained was filtered and crystallized from ethanol to give title compound, was identified by spectroscopic data. m.p. 160–162° C. $^1$H NMR (CDCl$_3$+DMSO-d6): 1.30 (d, 3H, J=6.8 Hz), 2.25 (s, 3H), 2.38 (s, 3H), 4.50 (1, 1H, J=6.8 Hz), 6.52 (dd, 1H, J=7.5 & 2.1 Hz), 6.70 (d, 1H, J=2.1 Hz), 7.10 (dd, 1H, J=7.5 & 0.8 Hz), 7.18 (d, 2H, J=7.5 Hz), 7.60 (d, 2H, J=7.5 Hz), 9.40 (brs, 1H), 10.22 (brs, 1H).

EXAMPLE 7

1-(2',4-Dichlorophenoxy)propionoyl-2-phenylsulfonylhydrazine

To a stirred solution of 2,4-dichlorophenoxypropionic acid hyudrazide in hot dry pyridine, benezenesulfonyl chloride was added dropwise. The reaction contents were refluexed for 7 hours and cooled. The crude reaction product was separated, when the reaction mixture was poured over crushed ice. It was filtered, washed with water and dried. The product was crystallized from ethanol and its structure was confirmed by spectral data. m.p. 182–183° C. $^1$H NMR (CDCl$_3$+DMSO-d6): 1.38 (d, 3H, J=6.8 Hz), 4.56 (1, 1H, J=6.8 Hz), 6.70 (d, 1H, J=7.6 Hz), 7.10 (dd, 1H, J=7.4 & 2.1 Hz), 7.35 (d, 1H, J=2.0 Hz), 7.40–7.60 (m, 3H), 7.80 (d, 2H, J=7.6 Hz), 9.20 (brs, 1H), 10.10 (brs, 1H).

EXAMPLE 8

1-(2'-Dichlorophenoxy)propionoyl-2-(4"-chlorophenyl)sulfonyl Hydrazine 2,4-Dichlorophenoxypropionic acid hydrazide was dissolved in required amount of dry pyridine. R-Chlorobezenesulfonyl chloride was added slowly to the above solution while stirring. Then, the reaction mixture was refluxed for 8 hours, cooled and poured over crushed ice when the crude product was obtained. It was filtered, washed with water, dried and crystallized from ethanol to give the title compound structure of the product was confirmed by spectroscopic data. m.p. 190–192° C. $^1$H NMR (CDCl$_3$+DMSO-d6): 1.40 (d, 3H, J=6.7 Hz), 4.50 (1, 1H, J=6.6 Hz), 6.65 (d, 1H, J=7.5 Hz), 7.05 (dd, 1H, J=7.5 & 1.9 Hz), 7.10 (d, 2H, J=7.8 Hz), 7.35 (d, 1H, J=1.9 Hz), 7.60 (d, 2H, J=7.8 Hz), 9.05 (brs, 1H), 10.10 (brs, 1H).

EXAMPLE 9

1-(2',4'-Dichlorophenoxy)propionoyl-2-(4"-tolune)sulfonyl Hydrazine

To a solution of 2,4-dichlorophenoxypropionic acid hydrazide in dry pyridine, 4-tolunesulfonyl choloride was added slowly while stirring. The reaction mixture was refluxed for 5 hours, cooled and poured over crushed ice. Crude reaction product was filtered, dried and crystallized from ethanol to obtain title compound, which was identified by spectra data m.p. 176–177° C. $^1$H NMR (CDCl$_3$+DMSO-d6): 1.40 (d, 3H, J=6.8 Hz), 2.42 (s, 3H), 4.54 (q, 1H, J=6.8 Hz), 6.68 (d, 1H, J=7.5 Hz0, 7.08 (dd, 1H, J=7.4 & 2.1 Hz), 7.20 (d, 2H, J=7.8 Hz), 7.32 (d, 1H, J=2.0 Hz), 7.70 (d, 2H, J=7.8 Hz), 9.00 (brs, 1H) 10.10 (brs, 1H).

Hypoglycemic Activity:

Typical representative members of this invention have shown hypoglycemic activity for the first time both in normoglycemic and Streptozotocin induced diabetic rats compared to standard drug. The standard drug used in both the experimental animal evaluation is Glibenclamide. The experimental details are given below.

Hypoglycemic Activity in Normal Rats:

Wistar rats of either sex weighing 150–180 gms were fasted overnight and divided into control, standard and test groups each consisting of 6 rats. The standard drug, Glibenclamide, was administered in the dose of 5 mg/kg per oral to the rats. All test compounds were administered in the dose of 200 mg/kg per oral to the test groups. Both standard and test drugs were administered as 1% gum acacia suspension. Control group received vehicle only. Blood glucose levels were measured before drugs administration at 0 hr and at 1 hr, 2 hr, 4 hr and 6 hr after drugs administration. Percent reduction of blood glucose levels at different time intervals was calculated with reference to basal glucose levels. All the blood glucose estimations were done using GOD/POD method and were analyzed using Auto Blood Analyzer (Technicon RA-1000, Bayer Diagnostics, Ireland). The standard drug (Glibenclamide) has shown a percent inhibition of glucose 65.1 and all the test compounds (1 to 9 examples) have shown percent inhibition in range of 48.5 to 63.2 (FIG. 1)

Hypoglycemic Activity in Streptozotocin Induced Diabetic Rats:

Wistar rats of either sex weighting 150–180 gms were used in this study and were divided into control, standard and test groups each consisting of 6 rats. Basal glucose levels were taken for all rats. Diabetes was induced by administering Streptozotocin in the dose of 50 mg/kg intravenously to the rats in all the groups. After a period of 48 hrs glucose levels were again measured and rats that have shown glucose levels of 400±20 mg/dl were selected. Glibenclamide (1 mg/kg) and the test compounds (50 mg/kg) were administered as 1% gum acacia suspension daily for a period of 14 days. At the end of 14 days after the last dose, blood glucose levels were again measured and the percent reduction in blood glucose was measured for all the rats in all the groups with respect to the initial reading before drug administration. The standard drug has shown hypoglycemic activity expressed as percent inhibition of blood glucose levels as 68.2 whereas test compounds (examples 1–9) has shown hypoglycemic activity in the range of 43.5 to 59.3 (FIG. 2).

The Main Advantages of the Present Invention are:
1. The process is simple and is a single step reaction.
2. Raw material are cheap and the process does not require special chemicals.
3. The total reaction can be completed in a period of 5–8 hrs on lab scale.
4. Since the end product is a solid, this permits the pharmaceutical formulated to make solid oral dosage forms such as tablets, capsules, etc.
5. The compounds may be useful in the management of diabetes as these are potential hypoglycemics.

We claim:
1. 1-(aryloxy)propionoyl-2-arylsulfonyl hydrazine of the formula

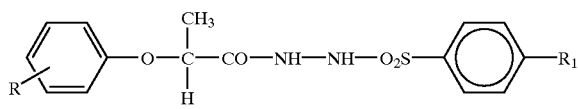

wherein R is selected from 4-Cl, 3-CH$_3$-4-Cl and 2,4-Cl$_2$, R$_1$ is selected from H, Cl, and CH$_3$.

2. 1-(aryloxy)propionoyl-2-arylsulfonyl hydrazine as claimed in claim 1 of the formula

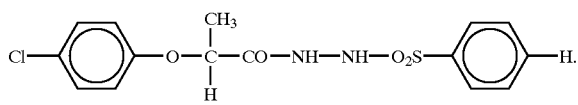

3. 1-(aryloxy)propionoyl-2-arylsulfonyl hydrazine as claimed in claim 1 of the formula

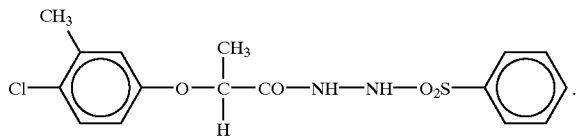

4. 1-(aryloxy)propionoyl-2-arylsulfonyl hydrazine as claimed in claim 1 of the formula

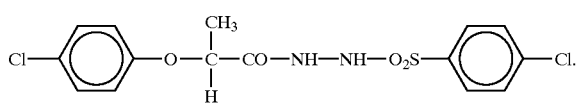

5. 1-(aryloxy)propionoyl-2-arylsulfonyl hydrazine as claimed in claim 1 of the formula

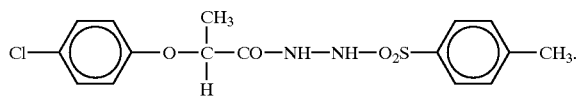

6. 1-(aryloxy)propionoyl-2-arylsulfonyl hydrazine as claimed in claim 1 of the formula

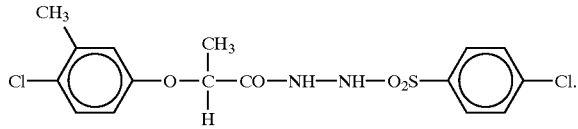

7. 1-(aryloxy)propionoyl-2-arylsulfonyl hydrazine as claimed in claim 1 of the formula

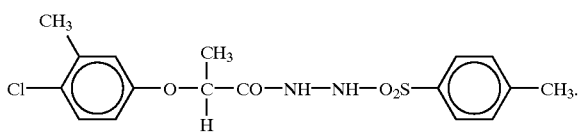

8. 1-(aryloxy)propionoyl-2-arylsulfonyl hydrazine as claimed in claim 1 of the formula

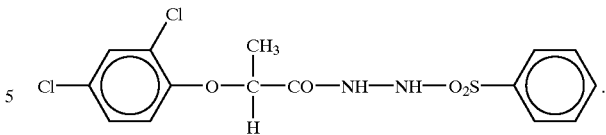

9. 1-(aryloxy)propionoyl-2-arylsulfonyl hydrazine as claimed in claim 1 of the formula

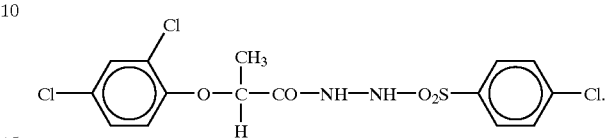

10. 1-(aryloxy)propionoyl-2-arylsulfonyl hydrazine as claimed in claim 1 of the formula

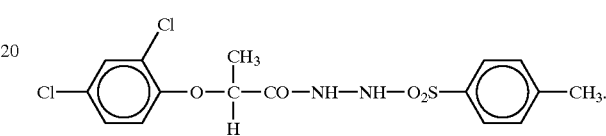

11. A process for the synthesis of 1-(aryloxy)propionoyl-2-arylsulfonyl hydrazines of the formula

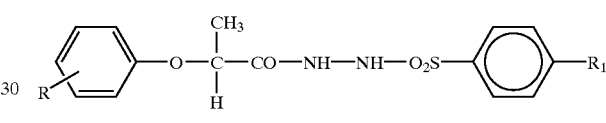

wherein R is selected from 4-Cl, 3-CH$_3$-4-Cl and 2,4-Cl$_2$, and R$_1$ is selected from H, Cl, and CH$_3$, which comprises reacting an aryloxypropionic acid hydrazide with an arylsulfonyl chloride.

12. A process as claimed in claim 11 wherein aryloxy is selected from the group consisting of 4-chlorophenoxy, 3-methyl-4-chlorophenoxy and 2,4-dichlorophenoxy groups.

13. A process as claimed in claim 11 wherein aryl is selected from the group consisting of phenyl, 4-chlorophenyl and 4-tolyl.

14. A method of treating hypoglycemia, which comprises administering, to a patient in need of such treatment, a dose effective amount of a 1-(aryloxy)propionoyl-2-arylsulfonyl hydrazine of the formula

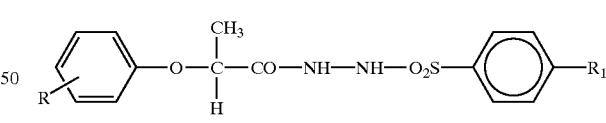

wherein R is selected from 4Cl, 3-CH$_3$-4Cl and 2,4-Cl$_2$, and R$_1$ is selected from H, Cl, and CH$_3$.

15. A method of treating hypoglycemia as claimed in claim 14, which comprises administering said 1-(aryloxy)propionoyl-2-arylsulfonyl hydrazine in a dose of from 50 to 200 mg per kilogram of body weight.

16. A process as claimed in claim 11, which comprises preparing a solution of aryloxypropionic acid hydrazine in dry pyridine and adding an arylsulfonyl chloride to said solution to form a reaction mixture.

17. A process as claimed in claim 16, which further comprises refluxing said reaction mixture for a time period of from 5 to 8 hours.

* * * * *